United States Patent [19]

Smit et al.

[11] Patent Number: 5,288,885
[45] Date of Patent: Feb. 22, 1994

[54] PURIFICATION OF TRI-ALKYL COMPOUNDS OF GROUP 3A METALS

[75] Inventors: Cornelis J. Smit; Gerbrand J. M. Van Eijden; Theodorus P. J. Peters; Pieter J. Reuvers, all of Arnhem, Netherlands

[73] Assignee: Shell Research Limited, London, United Kingdom

[21] Appl. No.: 971,875

[22] Filed: Nov. 5, 1992

[30] Foreign Application Priority Data

Nov. 19, 1991 [EP] European Pat. Off. ........ 91203016.0

[51] Int. Cl.$^5$ ............................ C07F 5/00; C07F 5/06
[52] U.S. Cl. ........................................ 556/1; 556/7; 556/187
[58] Field of Search ................... 556/1, 187, 7

[56] References Cited

FOREIGN PATENT DOCUMENTS

| 0148790 | 8/1984 | Japan | 556/187 |
|---|---|---|---|
| 2185090 | 8/1987 | Japan | 556/1 |
| 0466238 | 4/1976 | U.S.S.R. | 556/1 |

Primary Examiner—Paul J. Killos
Assistant Examiner—Porfirio Nazario

[57] ABSTRACT

A tri-alkyl compound of a Group 3a metal is purified by a process in which a polyether of the formula $$R-\left[O-\left(\underset{R'}{\underset{|}{CH}}\right)_m\right]_n-OR$$

wherein R independently is alkyl of 1 to 4 carbon atoms inclusive, each R' independently is hydrogen, methyl or ethyl; m is an integer from 1 to 6 inclusive; and n is an integer from 1 to 12 inclusive, is added to a composition comprising a tri-alkyl compound and the polyether. The adduct is heated to dissociate the adduct thermally into a mixture containing tri-alkyl compound of the Group 3a metal, and the mixture is subjected to distillation to recover the tri-alkyl compound of the Group 3a metal.

14 Claims, No Drawings

PURIFICATION OF TRI-ALKYL COMPOUNDS OF GROUP 3A METALS

FIELD OF THE INVENTION

The present invention relates to a process for the purification of tri-alkyl compounds of Group 3a metals. By "Group 3a metals" is mean aluminum, gallium, indium and thallium.

BACKGROUND OF THE INVENTION

Tri-alkyl compounds of Group 3a metals find increasing use in the electronics industry. In this industry the metals are deposited, alone or in combination with other elements, onto suitable substrates. Frequently, such metals are deposited as a compound with at least one Group 5a element such as phosphorus and/or arsenic. The deposition of these compounds is carried out by the decomposition of organometallic compounds from the vapor phase. Such decomposition is known as Metal Organic Chemical Vapor Deposition (MOCVD). When epitaxial layers are grown the technique is better known as the Metal Organic Vapor Phase Epitaxy (MOVPE). The organometallic compounds that are employed in the above techniques are usually alkyl compounds of the metals involved. The organometallic compounds used in this industry need to be very pure because small amounts of impurities may have a large effect on both the electrical and optical performance of the semiconductor layer deposited therefrom.

A method for the purification of Group 3a organometallic compounds is described in European patent application No. 372,138. According to this method an intermediate product of tri-alkyl compound of a Group 3a metal with a compound of another metal is formed. Since the intermediate product is essentially nonvolatile, all relatively volatile impurities can be removed. Subsequently, the desired Group 3a metal tri-alkyl compound is liberated from the intermediate product by adding a halide of the Group 3a metal. A disadvantage of this method is the introduction of another metal compound and possibly other and/or more impurities into the system. Because it is difficult to obtain the halides of Group 3a metals in a sufficiently pure form, the use of these halides necessarily introduces impurities.

Another method for purifying Group 3a organometallic compounds is disclosed in U.S. Pat. No. 4,720,561, in which method an adduct of a tri-alkyl compound is prepared using an aryl containing Group 5 ligand. A preferred species of such ligands is 1,2-bis(diphenylphosphino)ethane. Use of these types of compounds may result in significant amounts of Group 5 element being found in the final product.

In U.K. patent specification No. 2,123,423 the purification of tri-alkyl gallium is described. In this purification a relatively involatile adduct of tri-alkyl gallium with a high-oiling ether is formed and subsequently volatile impurities are removed therefrom. The adduct is then thermally dissociated to yield the ether and the purified tri-alkyl gallium. As suitable ethers di-isopentyl ether and diphenyl ether are mentioned. In one example the preparation of trimethyl gallium is described using di-isopentyl ether. The result is a relatively pure trimethylgallium product.

It would be of advantage, however, to provide a method for the purification of tri-alkyl compounds of Group 3a metals wherein a product of excellent purity is obtained.

SUMMARY OF THE INVENTION

The present invention provides a process for the purification of a tri-alkyl compound of a Group 3a metal in which process a polyether of the formula

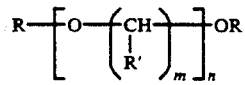

wherein R independently is an alkyl group with 1 to 4 carbon atoms; each R' is independently selected from the group consisting of hydrogen, methyl or ethyl, m is an integer from 1 to 6, and n is an integer from 1 to 12, is added to a tri-alkyl compound of a Group 3a metal to obtain an adduct of the tri-alkyl compound and the polyether. The adduct is heated to dissociate the adduct thermally into a mixture containing dissociated tri-alkyl compound of the Group 3a metal and the resulting mixture is subjected to distillation to recover the dissociated tri-alkyl compound of the Group 3a metal.

DESCRIPTION OF THE INVENTION

The use of the polyether of the invention enables the obtaining of a very pure product. Although it is not intended to be bound by any theory, it is believed that the polyether having $n+1$ oxygen atoms per molecule forms an adduct with a number, generally up to n, of tri-alkyl metal compounds. Upon heating at least a portion of the adduct thermally dissociates, releasing the pure tri-alkyl compound. Upon distillation the pure tri-alkyl compound is recovered as an overhead product.

To facilitate the separation during distillation the R and R' groups and m and n are suitably selected such that there is a substantial difference in boiling points between the polyether and the tri-alkyl compound to be purified. Such a substantial difference is suitably from about 50° C. to about 150° C. For practical reasons, the number n of oxyalkylene groups in the polyether is preferably from 2 to 8 inclusive, and more preferably from 2 to 4 inclusive, R is alkyl of 1 to 4 carbon atoms inclusive. Preferably, R is methyl or ethyl. The integer m is from 1 to 6 inclusive. Preferably, m is from 2 to 4 inclusive. The R' group at each carbon atom independently is hydrogen, methyl or ethyl. When m>1, preferably not more than one R' is other than hydrogen. The oxyalkylene group in the polyether is preferably oxyethylene. In this embodiment m represents 2 and each R' is hydrogen. Diglyme (diethylene glycol dimethyl ether), triglyme (triethylene glycol dimethyl ether) or tetraglyme (tetraethylene glycol dimethyl ether) are illustrative of the most preferred polyethers.

The metals of Group 3a of the Periodic Table of the Elements that are employed in MOCVD or MOVPE are aluminum, gallium and indium. These metals are preferred in the present process. The alkyl groups in the tri-alkyl compounds may be straight-chain or branched. Although the present process can be carried out with a wide variety of tri-alkyl compounds, including those having long chain alkyl groups, the purification of tri-alkyl compounds containing alkyl groups of up to 6 carbon atoms inclusive is preferred. More preferably, the alkyl group in the tri-alkyl compound has from 1 to 4 carbon atoms inclusive. Most preferably, the alkyl is methyl or ethyl.

The mixture containing the tri-alkyl compound of the Group 3a metal to be purified contains other constituents, such as impurities. It is preferred to employ the instant invention for compositions having a relatively small amount of impurities. The process is useful for purifying mixtures of trialkyl compounds of Group 3a metal containing as high as about 5% by weight of impurities or as low as about 10 ppm (parts per million by weight) of impurities.

The adduct of the tri-alkyl compound with the polyether according to the invention is obtained by mixing the relatively impure tri-alkyl compound with the polyether and allowing the adduct to form. The formation of the adduct starts instantaneously upon addition. The formation can be carried out at any convenient temperature. Useful temperatures are from about −20° C. to about 250° C.

On occasion, the impure composition to be purified is initially mixed with a monoether to form an initial adduct of the tri-alkyl compound and the monoether. The adduct with the polyether is then prepared by displacing the monoether from the earlier-formed adduct by mixing with the polyether. When the monoether in the intermediate adduct is more volatile than the polyether, the substitution is facilitated by distilling off the released monoether, thereby shifting the equilibrium of the displace reaction in favor of the formation of the adduct with the polyether. The monoether to be employed in this embodiment is selected from a wide variety of monoethers. Suitable monoethers include ethers of the formula R″—O—R″, in which R″ independently is alkyl of up to 8 carbon atoms inclusive, preferably from 2 to 6 carbon atoms inclusive. Preferred monoethers are diethyl ether, di-isopropyl ether and di-isopentyl ether.

The amount of polyether to be employed relative to the tri-alkyl compound is variable but it is preferred that the amount of polyether selected be such that all tri-alkyl compound present forms an adduct with the polyether. It should be recognized that it is possible to form adducts comprising one molecule of polyether with more than one molecule of tri-alkyl compound. For reasons of convenience, molar excess of polyether with respect to the number of oxygen atoms is usually employed. Generally, the amount of polyether added to the composition comprising the tri-alkyl compound ranges is no more than about 10 moles of polyether per mole of tri-alkyl compound. Preferably, the amount of polyether is from about 0.1 mole to about 10 moles of polyether per mole of tri-alkyl compound. The adduct is separated and recovered from the media of its production by conventional methods such as distillation or extraction.

The pure tri-alkyl compound is recovered by distillation of the mixture of tri-alkyl compound and polyether after the recovered adduct is dissociated. In a preferred embodiment, the adduct is heated to effect the dissociation, and the dissociated tri-alkyl compound is simultaneously distilled off. In order to prevent the distillation temperature of the mixture from rising above the decomposition temperature of the tri-alkyl compound, the distillation is preferably carried out at reduced pressure. Such pressure is suitably below about 250 mbar. The pressure may be as low as below about 0.1 mbar.

In the distillation of the tri-alkyl compound of the Group 3a metal from the mixture by distillation it is often advantageous to recover the first 1 to 10 percent by volume of the product separately. In such case the fraction that is subsequently recovered as the desired product has an enhanced purity. The first fraction of the distilled product is recycled to the original reaction mixture for further use or is discarded. In addition, the distillation residue is often recycled. This is especially desirable when the dissociation of the adduct of tri-alkyl compound and polyether is only partial and the residue therefore still contains a significant amount of tri-alkyl compound.

The invention will be further illustrated by the following examples and comparative experiments, which should not be regarded as limiting.

EXAMPLE 1

The Purification of Trimethyl Aluminum

In a flask 751 g of distilled trimethyl aluminum (TMA) was added to 549 g diglyme at such a rate that the temperature did not exceed 100° C. The mixture was stirred overnight at 100° C. The pressure was lowered to 150 mbar and the bottom temperature increased to 150° C. Pure trimethylaluminum.diglyme adduct was recovered as the overhead fraction at a distillation temperature of 158° C. (10 mbar).

A 2 liter flask was charged with 1016 g of this adduct and 265 g of distilled TMA was added at such a rate that the temperature rose to 60° C. After the addition was complete, the contents in the flask solidified. The flask was then equipped with a fractionating column and the pressure was lowered to 100 mbar and the flask temperature was increased to 90° C. At a distillation head temperature of 58° C. TMA was distilled over and collected in fractions. The yield of pure TMA product was 72% based on the TMA added to the trimethylaluminum.diglyme adduct. The residue consisted quantitatively of the adduct.

The purity of the TMA recovered is illustrated by its silicon content. The silicon content in the recovered TMA was 0.1 ppm, relative to a volatile TMS (tetramethyl silane) standard, whereas the silicon content in the distilled TMA added to the adduct was 0.4 ppm. The silicon impurities were determined by inductively coupled plasma-optical emission spectroscopy (ICP-OES). No other elemental impurities were detected.

EXAMPLE 2

The Purification of Triethylgallium

A triethylgallium (TEG) adduct with diethyl ether was prepared by adding ethyl bromide to a gallium-magnesium alloy ($GaMg_2$) in a mixture of diphenyl ether and diethyl ether. The reaction was exothermic and the rate of ethyl bromide addition was such that the reaction temperature did not exceed 140° C. After all ethyl bromide was added the reaction mixture was stirred for 16 hours at 100° C. to yield a TEG diethyl ether adduct. Subsequently, this adduct was distilled at a bottom temperature of 100°–140° C. and at decreasing pressure (from 1000 mbar to 25 mbar) to maintain the distillation rate.

Tetraglyme (1171 g) was then added to the distilled TEG·diethyl ether adduct. The molar ratio of TEG to tetraglyme was 1.6:1. Subsequently, the diethyl ether was removed at 1 mbar and room temperature over 16 hours, yielding crude $TEG_{1.6}$·tetraglyme adduct. The silicon content of this adduct was 0.5 ppm, as determined by ICP-OES, using TMS as standard.

This crude adduct was heated to 121°–150° C. at 30 mbar, thereby dissociating the TEG from the adduct and simultaneously distilling the dissociated TEG. The dissociated TEG was completely free of diethyl ether as determined by $^1$H-NMR. The silicon content in the dissociated TEG was <0.1 ppm, as determined by ICP-OES, using TMS as standard. No other impurities were detected.

EXAMPLE 3

The Purification of Trimethylindium

An adduct of trimethylindium (TMI) and diethyl ether was prepared by adding a solution of methylmagnesium iodide in diethyl ether to a solution of indium (III) chloride in diethyl ether. After addition, the mixture was stirred for 3 hours at 100° C. and for 16 hours at room temperature. The TMI·diethyl ether adduct was obtained by distillation which gave a fraction boiling between 133° C. and 135° C. The yield was 51%, based on indium chloride.

To the TMI·diethyl ether adduct an amount of tetraglyme was added to give a molar ratio of TMI to tetraglyme of 2.5:1. Diethyl ether was distilled off and the distillation was stopped at a bottom temperature of 100° C. at ambient pressure. Last traces of diethyl ether were removed in vacuo thereby yielding a TMI$_{2.5}$·tetraglyme adduct. This adduct was transferred to a 500 ml flask and was dissociated to obtain the free TMI by heating at a temperature of 160° C. and reduced pressure. The residue, containing TMI and tetraglyme, was recycled. The TMI obtained was further purified by sublimation.

The purity is illustrated by the silicon and magnesium contents. Whereas the TMI·diethyl ether adduct contained 2 ppm silicon and 7.7 ppm magnesium, the purified TMI contained <0.05 ppm silicon and 0.01 ppm magnesium. No other impurities were detected by ICP-OES.

EXAMPLE 4

Purification of Trimethylindium

By a procedure substantially similar to that of Example 3 TMI·diethyl adduct was treated with triglyme. After separation of diethyl ether, a TMI$_2$·triglyme adduct was obtained. The adduct was dissociated by distillation as described in Example 3 and TMI was thereby obtained.

EXAMPLE 5

Purification of Triethylindium

By a procedure substantially similar to that of Example 3, an adduct of triethyl indium (TEI) and diethyl ether was prepared from indium (III) chloride and ethyl magnesium iodide. To this adduct sufficient tetraglyme was added to give a molar ratio of TEI to tetraglyme was 3:1. Diethyl ether was removed in vacuo at a bottom temperature of 74° C. Subsequently, pure TEI was obtained via dissociation of the adduct at 74°–115° C. and a pressure of <1 mbar. The TEI thereby obtained was subsequently subjected to fractional distillation at a pressure of <1 mbar. No metal impurities could be detected by ICP-OES in the distilled TEI.

COMPARATIVE EXPERIMENT 1

Use of Dibenzyl Ether 30 g of an InMg$_3$ alloy was reacted with 120 g methyl iodide under an atmosphere of purified argon, using a mixture of dibenzyl ether and diethyl ether as solvent. After stirring overnight the reaction mixture was grey-white. After settling of the solids, the liquid was decanted. The bottom temperature of the trimethylindium-containing phase was gradually increased and at a temperature of 200° C. decomposition of the contents of the flask occurred. No TMI was distilled.

COMPARATIVE EXPERIMENT 2

Use of Di-Isopentyl Ether

By a procedure substantially similar to that of Comparative Experiment 1, InMg$_3$ alloy was reacted with methyl iodide, but now using a mixture of diethyl ether and di-isopentyl ether as solvent. After addition of the methyl iodide the mixture was stirred overnight at a temperature of 95° C. Subsequently, the diethyl ether was distilled off at atmospheric pressure and a bottom temperature of 190° C. Then the pressure was lowered to <1 mbar and a trimethylindium-containing product was collected. The product consisted of a trimethylindium.di-isopentyl ether adduct (molar ratio 5:1).

What is claimed is:

1. A process for the purification of tri-alkyl compound of Group 3a metal selected from the group of aluminum, gallium, indium and thallium by adding (i) a polyether of the formula

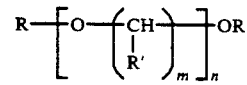

wherein R independently is alkyl of 1 to 4 carbon atoms inclusive, R' independently is hydrogen, methyl or ethyl, m is an integer from 1 to 6 inclusive and n is an integer from 1 to 12 inclusive, to (ii) an impure mixture comprising a tri-alkyl compound of said Group 3a metal, thereby obtaining an adduct of the tri-alkyl compound and the polyether, heating the adduct to produce tri-alkyl compound of said Group 3a metal; and recovering the tri-alkyl compound of said Group 3a metal by distillation.

2. The process of claim 1 wherein R is methyl or ethyl.

3. The process of claim 2 wherein R' is hydrogen.

4. The process of claim 3 wherein n is an integer from 2 to 4 inclusive.

5. The process of claim 4 wherein m is an integer from 2 to 4 inclusive.

6. The process of claim 2 wherein R' is methyl.

7. The process of claim 1 wherein the alkyl of the trialkyl compound is alkyl of from 1 to 6 carbon atoms inclusive.

8. The process of claim 7 wherein R is methyl or ethyl.

9. The process of claim 8 wherein R' is hydrogen.

10. The process of claim 8 wherein R' is methyl.

11. The process of claim 9 wherein the alkyl of the tri-alkyl compound is methyl.

12. The process of claim 9 wherein the alkyl of the tri-alkyl compound is ethyl.

13. The process of claim 7 wherein the Group 3a metal is indium.

14. The process of claim 12 wherein the Group 3a metal is indium.

* * * * *